(12) United States Patent
Benner

(10) Patent No.: US 6,627,456 B1
(45) Date of Patent: Sep. 30, 2003

(54) METHOD FOR SELECTING FUNCTIONAL DEOXYRIBONUCLEOTIDE DERIVATIVES

(76) Inventor: Steven Albert Benner, 1501 NW. 68th Ter., Gainesville, FL (US) 32605

( * ) Notice: Subject to any disclaimer, the term of this patent is extended or adjusted under 35 U.S.C. 154(b) by 0 days.

(21) Appl. No.: 09/415,966

(22) Filed: Oct. 12, 1999

Related U.S. Application Data

(63) Continuation of application No. 08/775,402, filed on Dec. 31, 1996, now Pat. No. 5,965,364, which is a continuation-in-part of application No. 08/542,142, filed on Oct. 12, 1995, now Pat. No. 6,037,120, and a continuation-in-part of application No. 08/375,132, filed on Jan. 17, 1995, now Pat. No. 6,001,983, which is a continuation of application No. 07/594,290, filed on Oct. 9, 1990, now Pat. No. 5,432,272.

(51) Int. Cl.$^7$ ................. G01N 33/566; C12P 19/34; C07H 21/02; C07H 21/04
(52) U.S. Cl. ............... 436/501; 435/91.1; 435/91.2; 536/22.1; 536/25.24; 536/25.3; 536/25.4
(58) Field of Search .................. 436/501; 435/91.1, 435/91.2, 6, 7.21, 7.2; 536/22.1, 25.24, 25.3, 25.4; 530/350

(56) References Cited

U.S. PATENT DOCUMENTS

| | | | |
|---|---|---|---|
| 4,683,202 A | 7/1987 | Mullis et al. | 435/91.2 |
| 5,270,163 A | 12/1993 | Gold et al. | 435/6 |
| 5,472,841 A | 12/1995 | Jayasena et al. | 435/6 |
| 5,476,766 A | 12/1995 | Gold et al. | 435/6 |
| 5,965,364 A | * 10/1999 | Brenner | 435/6 |

OTHER PUBLICATIONS

Piccirilli et al. (1990) *Nature* 343:33–37.
Szoskak (1992) *Trends in Biochem* 17:89–93.
Switzer et al. (1993) *Biochem.* 32:10489–10496.
Gibson, K.J. et al. (1987) *Nucleic Acids Res.* 15(16):6455–6467.
Cruickshank, K.A. et al. (1988) *Tetrahedron Lett.* 29(41):5221–5224.
Voegel, J.J. et al. (1996) *Helvetica Chimica Acta* 79:1863–1880.
Voegel, J.J. et al. (1996) *Helvetica Chimica Acta* 79:1881–1893.
Irvine, D. et al. (1991) *J. Mol. Biol.* 222:739–761.
Zimmer C. (1975) *Prog. Nucl. Acid Res. Mol. Biol.* 15:285–318.
Stirchak, E.P. (1989) *Nucl. Acids Res.* 17(15):6129–6141.
Folsom, V. et al. (1989) *Analytical Biochem.* 182:309–314.
Benner, S.A. et al. (1988) *CRC Critical Reviews in Biochem.* 23(4):369–426.
Chen, H. et al. (1994) *Biochemistry* 33:8746–8756.
Ekland, E.H. et al. (1996) *Nature* 382:373–376.
Voegel, J.J. et al. (1994) *J. Am. Chem. Soc.* 116:6929–6930.
Voegel, J.J. et al. (1993) *Helvetica Chimica Acta* 76:2061–2069.
Khym, J.X. et al. (1963) *Biochemistry* 2(2):344–350.
Crisp, G.T. (1993) *J. Org. Chem.* 58:6614–6619.
Ludwig, J. et al. (1989) *J. Org. Chem.* 54:631–635.
Casalnuovo, A.L. et al. (1990) *J. Am. Chem. Soc.* 112:4324–4330.
Hobbs, F.W., Jr. (1989) *J. Org. Chem.* 54:3420–3422.
Robbins, M.J. et al. (1983) *J. Org. Chem.* 48:1854–1862.
Robbins, M.J. et al. (1990) *Tetrahedron Lett.* 31(26):3731–3734.
Haralambidis, J. et al. (1987) *Nucl. Acids. Res.* 15(12):4857–4877.
Brown et al. (1965) *J. Chem. Soc.* pp. 5072–5074 [there is no vol. No. used for this journal].

* cited by examiner

*Primary Examiner*—Stephanie W. Zitomer

(57) ABSTRACT

Improvements are disclosed for in vitro selection methods that yield ligands and catalysts through partitioning libraries of oligonucleotides. These improvements all increase the diversity and amount of fuctionality available to the oligonucleotides, by incorporating into the oligonucleotide libraries non-standard nucleobase analogs and/or functionalized standard nucleobases, and/or incorporating into the selection mixture organic cofactors that deliver functional groups by binding non-covalently to oligonucleotides in the library.

4 Claims, 3 Drawing Sheets

METHOD FOR SELECTING FUNCTIONAL DEOXYRIBONUCLEOTIDE DERIVATIVES

CROSS REFERENCE TO RELATED APPLICATIONS

Figure 1:
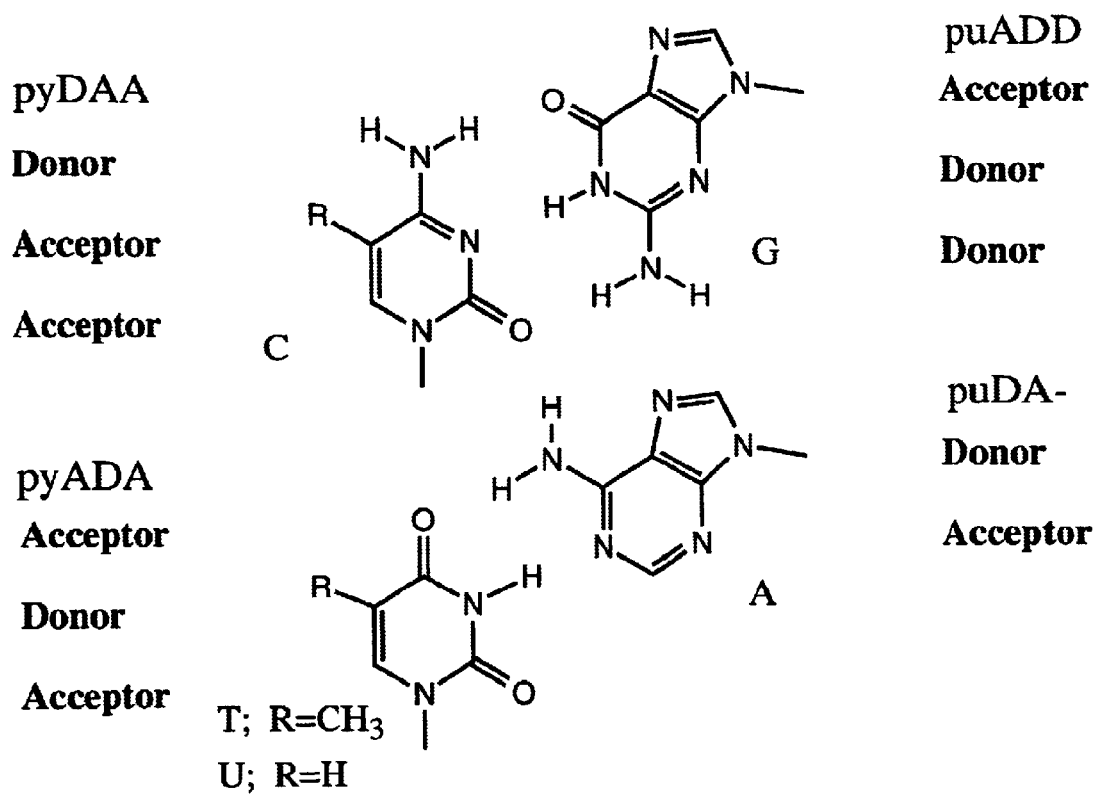

This application is a continuation of application Ser. No. 08/775,402 filed Dec. 31, 1996, now U.S. Pat. No. 5,965,364 which is a continuation-in-part of applications Ser. No. 08/542,142 filed Oct. 12, 1995, now U.S. Pat. No. 6,037,120, and application Ser. No. 08/375,132 filed Jan. 17, 1995, now U.S. Pat. No. 6,001,983, which application is a continuation in part of application Ser. No. 07/594,290 filed Oct. 9, 1990, now issued as U.S. Pat. No. 5,432,272, the disclosures of which are herein incorporated by reference. Related applications include Ser. No. 08/094,363 now abandoned.

Statement of rights to inventions made under Federally-sponsored research: None

INTRODUCTION

1. Field of the Invention

This invention pertains to the field of nucleic acid chemistry, and to combinatorial chemistry as it is applied to nucleic acids. More specifically, the invention concerns procedures for obtaining oligonucleotides and their analogs that can serve a function, most preferably as ligands, receptors, and catalysts. More specifically, this invention relates to methods for selecting in vitro oligonucleotide derivatives that can serve as ligands, receptors, or catalysts, starting from a pool of oligodeoxyribonucleotide derivatives that incorporate non-standard nucleobases, or incorporate standard nucleobases modified to carry additional functional groups, or standard oligonucleotides acting in conjunction with organic cofactors.

2. Background of the Invention

The majority of pharmaceutical agents are compounds that exert their biological activity by binding to a biological macromolecule, referred to here as a receptor. The discovery of ligands that can bind to a preselected receptor and thereby exert a biological effect is an important goal of medicinal chemists seeking to develop new human pharmaceutical agents.

Classically, ligands are discovered by three strategies. The first involves screening of a collection of chemicals whose structures have no deliberate connection with the structure or biology of the target receptor. This process is referred to as "random screening".

The second strategy requires information about the structure of the natural ligand for a receptor. Development of new ligands then is based on the deliberate synthesis of specific analogs of the natural ligand in the hope of discovering a ligand that retains or has increased affinity for the receptor, together with bioavailability, stability, and other properties desired for a human pharmaceutical.

The third strategy requires information about the structure of the receptor itself. With this information, ligands are designed by the design of structures that are complementary to the binding site of the ligand.

The deficiencies of these three approaches are well known to those familiar with the art. Random input screening often requires examination of thousands of compounds before a single ligand has a chance of being identified. Analogs of the natural ligands often resemble the natural ligand in terms of bioavailability, stability, or other properties; often, these properties are undesirable in a human pharmaceutical. Further, while tremendous strides have been made in the science of molecular recognition over the past decade, it is still not possible to design a ligand for a receptor even given a high resolution experimental structure for the receptor itself.

One approach suggested for solving these problems comes under the title of "in vitro selection". The approach has several implementations. Most commonly, a collection, or library, of oligonucleotides of random sequence is presented to a receptor, often attached to a solid support. The receptor binds to only a few oligonucleotides in the library. The oligonucleotides in the pool that do not bind to the receptor are then washed from the receptor. The oligonucleotides that bind to the receptor tightly are then eluted from the receptor and recovered. These are then amplified by polymerase chain reaction technology, well known in the art (Mullis et al., U.S. Pat. No. 4,683,202), to yield a library of oligonucleotides whose members have a higher affinity, on average, than the members of the original pool. This new library is then subjected to mutation by methods well known in the art to create a new library of oligonucleotides with structures randomized around those of the starting library with increased affinity for the receptor. These are then subjected to the binding, elution, and amplification steps in repeated cycles, leading to oligonucleotides with increased binding activity. After several rounds of selection, a secondary library can next be prepared from a mixture of oligonucleotides already enriched with those that have affinity for a receptor, by amplifying the mixture using polymerases under conditions where the polymerase makes mistakes. The secondary library re-diversifies the library of ligands that already has some affinity to the receptor, permitting the in vitro selection experiment to search a region of combinatorial "sequence space" (Benner, S. A., Ellington, A. D. (1988) *CRC Crit. Rev. Biochem.* 23, 369–426) that is likely to contain oligonucleotides with the desired properties.

Those of ordinary skill in the art understand both the value of in vitro selection, and how to perform its individual steps in the laboratory. Preparation of mixtures of oligonucleotides, affinity purification of ligands from a mixture containing both ligands and non-ligands, amplification of oligonucleotides by PCR, and the mutagenesis of oligonucleotides are all well known in the art. In vitro selection has been recognized as being useful for obtaining ligands, receptors, and catalysts by many groups. Early articles by Joyce (Joyce, G. F. (1989) in RNA: Catalysis, Splicing, Evolution, Belfort and Shub, eds. Elsevier, Amsterdam, pp. 83–87), Irvine et al. (Irvine, D., Tuerk, C., Gold, L. (1991) *J. Mol. Biol.* 222, 739–761), and Szostak (Szostak, J. W. (1992) *Trends Biochem. Soc.* 17, 89–93) layed out the elements of classical in vitro selection methodologies. For example, in vitro selection was used to obtain oligonucleotides as ligands for reverse transcriptase by Chen et al. (Chen, H., Gold, L. (1994) *Biochemistry* 33, 8746–8756). In the patent literature, Gold and Tuerk (U.S. Pat. No. 5,270,163) propose in vitro selection methods on RNA libraries as an approach towards obtaining ligands and receptors. Gold (U.S. Pat. No. 5,476,766) propose an in vitro selection system for amplifying RNA to create ligands for thrombin. Jayasena and Gold (U.S. Pat. No. 5,472,841) consider oligonucleotide libraries where the 2'-hydroxyl group of the ribose ring of standard oligonucleotides may be replaced by a 2'-amino group. In principle, when selection methods permit enrichment of oligonucleotides that bind to a transition state analog, catalysts might also be obtained by in vitro selection (U.S. Pat. No. 5,270,163).

It is clear that in vitro selection based on natural oligonucleotides has limited efficacy, however. As discussed in Ser. No. 07/594,290, filed: Oct. 9, 1990, now issued as U.S. Pat. No. 5,432,272, of which the instant application is a continuation-in-part, the primary difficulty with in vitro selection as a tool for creating molecules with desired properties arises from the fact that natural oligonucleotides do not themselves display a wide diversity in either structure, or conformation, or functionality. Oligonucleotides that form the libraries used in classical in vitro selection experiments are built from only four building blocks. These building blocks carry relatively little useful functionality, especially compared to that carried by proteins. Thus, oligonucleotides with tight affinity for some receptors occur only infrequently in a population of random oligonucleotides. This makes it difficult to identify oligonucleotides within a library of standard oligonucleotide sequences that have satisfactory binding or catalytic properties for a range of ligands and reactions.

SUMMARY OF THE INVENTION

The instant invention provides improvements to classical in vitro selection methods already known in the art, to increase the effectiveness of in vitro selection experiments as a tool for generating new structures (e.g., bent oligonucleotides), ligands, receptors, and catalysts. The improvements comprise incorporating into the oligonucleotide analogs that are the components of a library to which in vitro selection methods functionalized standard nucleotides and non-standard nucleotides, both functionalized and not functionalized, and incorporating functionalized cofactors into the in vitro selection experiment.

BRIEF DESCRIPTION OF THE DRAWINGS xxx

FIG. 1 shows the two standard base pairs formed between the standard bases, e.g. C and G; T and A. To systematize the nomenclature for standard nucleobases, pyrimidines are designated by the prefix "py", purines by the prefix "pu". Following the prefix is the order, from the major groove to the minor groove, of acceptor (A) and donor (D) groups. Thus, both thymine and uracil implement the standard hydrogen bonding pattern pyADA. The standard nucleobase cytosine implements the standard hydrogen bonding pattern pyDAA. The standard nucleobases adenine and guanine implement the standard hydrogen bonding pattern puDA- and puADD respectively.

Figure 2:
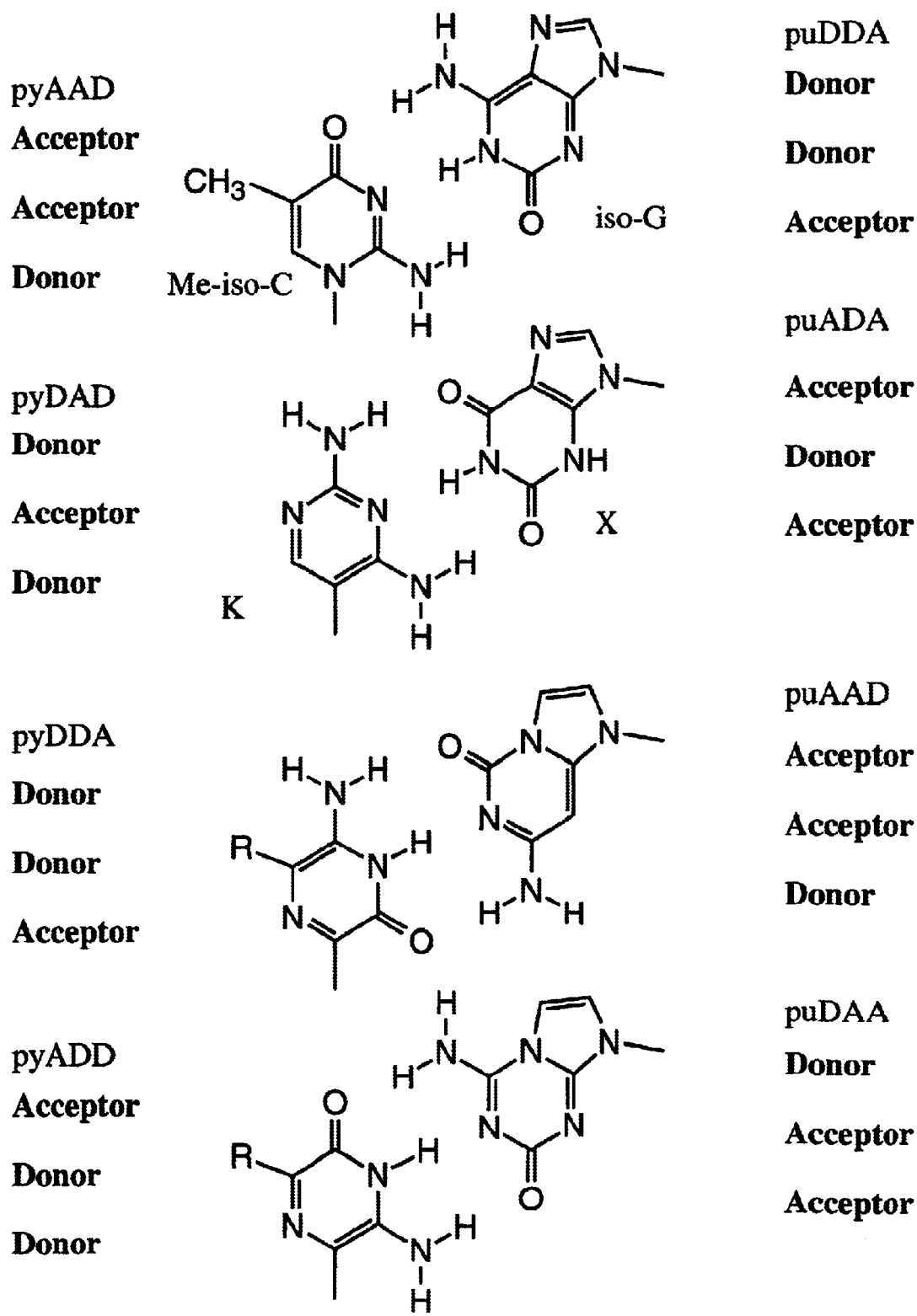

FIG. 2 shows the specific structures of eight different base pairs that include the preferred embodiments according to the subject invention. To systematize the nomenclature for non-standard nucleobases, pyrimidines are designated by the prefix "py", purines by the prefix "pu". Following the prefix is the order, from the major groove to the minor groove, of acceptor (A) and donor (D) groups.

Figure 3:
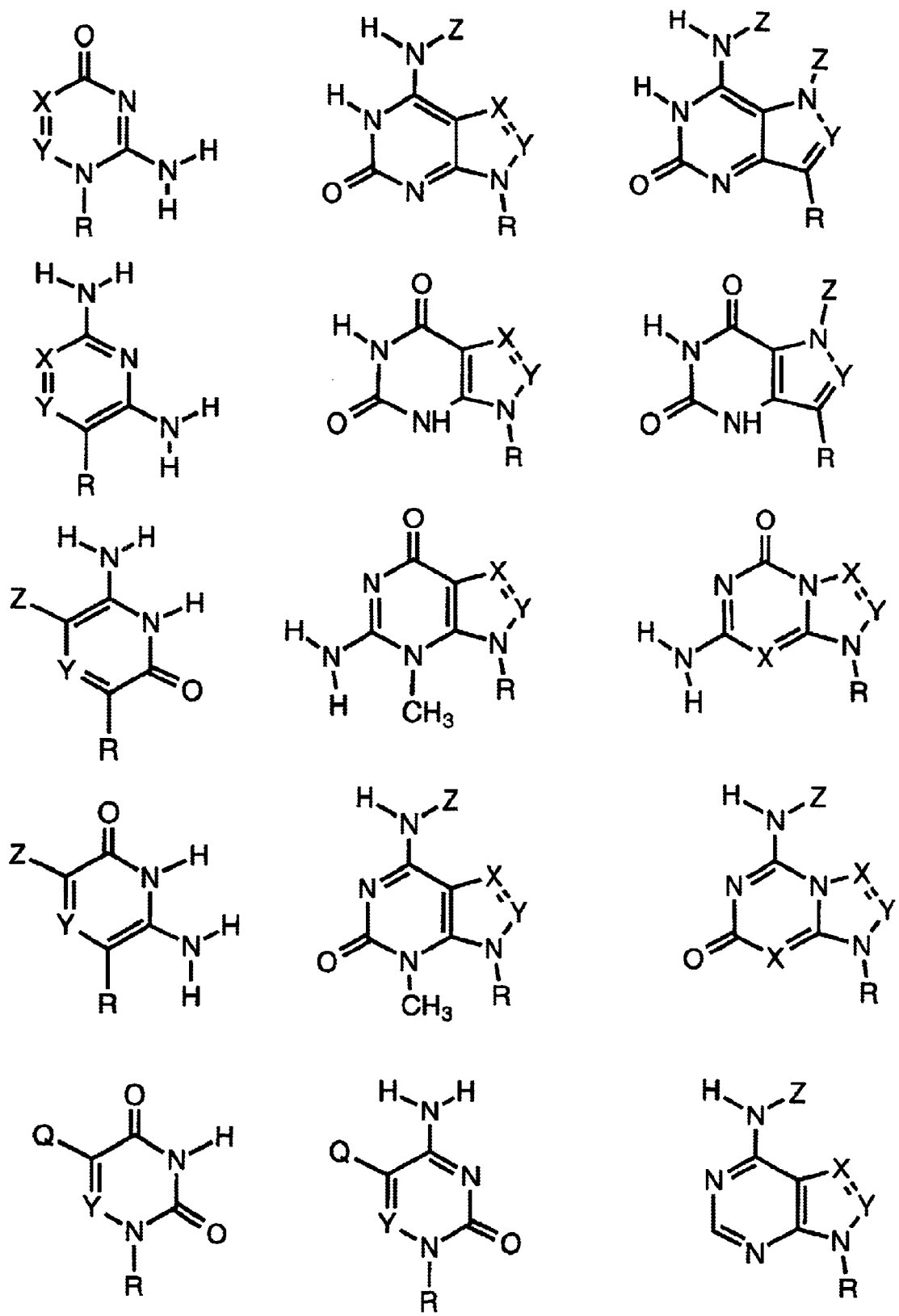

FIG. 3 shows the general structures of eight different base pairs according to the subject invention. The notation -R designates the point of attachment of the ribose, deoxyribose, or ribose or deoxyribose derivative, X is either a nitrogen atom or a carbon atom bearing a substituent Z, Z is either a hydrogen, an unfunctionalized lower alkyl, alkynyl, or alkyl-alkynyl chain, or a lower alkyl, alkynyl, or alkyl-alkynyl chain bearing an amino, trifluoroacetamido, carboxyl, hydroxy, thiol, aryl, indole, or imidazoyl group, Y is either N or CH, and the ring contains no more than three nitrogens consecutively bonded.

DETAILED DESCRIPTION OF THE INVENTION AND PREFERRED EMBODIMENTS

Three approaches might be envisioned to circumvent limitations of in vitro selection systems that are intrinsic in the limitations in the structure of conventional oligonucleotides built fully from conventional nucleotides (ribo or deoxyribo adenylic acid, guanylic acids, and cytidylic acid, and uridylic acid or thymidylic acid, referred to by convention as A, G, C, T and U). The first is based on an understanding of how complementary oligonucleotides recognize each other, and how complementarity is used in polymerase chain reaction amplification of oligonucleotides during an in vitro selection cycle. The invention disclosed in Ser. No. 08/375,132 (filed Jan. 17, 1995, for "In vitro Selection with Non-standard Bases") discloses an invention where the number of nucleobase building blocks that can be incorporated and independently replicated in an oligonucleotide analog is increased, where the additional nucleobases present non-standard patterns of hydrogen bonding groups to a complementary strand, and therefore can be independently copied in a polymerase chain reaction (PCR). In this context, "non-standard" refers to the pattern of hydrogen bonds that holds a nucleobase to its complement in a complementary strand in a Watson-Crick geometry. The non-standard nucleobases confer additional function on an oligonucleotide analog not found in a conventional oligonucleotide.

The second involves the addition of "cofactors" to the library. Cofactors are defined here to mean low molecular weight substances that carry one or more functional groups, and that bind either covalently (for example, through an imine linkage or a disulfide bond) or non-covalently to an oligonucleotide and deliver the valuable functionality to a non-covalent complex between the cofactor and the oligonucleotide. Cofactors are distinct in that they are not encoded in the oligonucleotide, and therefore the information concerning their structure is not amplified during a PCR cycle. Cofactors are well known in protein chemistry. For example, natural protein polymers do not contain amino acids that have aldehyde or ketone functionality, a redox active center, or a unit that can perform Umpolung chemistry. This means that proteins have an intrinsically low ability to catalyze reactions that require these functionalities. Natural proteins circumvent this limitation by using the cofactors pyridoxal phosphate, flavin adenine dinucleotide, and thiamine, respectively, small molecules that bind non-covalently to a protein built with standard amino acids, and once bound, provide the functionality missing in the building blocks of a standard protein. The binding and catalytic potential of oligonucleotides can also be improved by the use of cofactors, and cofactors can be designed to facilitate their non-covalent interactions with oligonucleotides.

Last, additional functionality can be introduced into an oligonucleotide by covalently attaching this functionality to standard nucleotides. This requires that a modified oligonucleotide ("modified" because it differs from a natural oligonucleotide by carrying appended moieties not found in natural oligonucleotides) be built to include nucleoside units that are modified, or derivatized, to carry functionality on the nucleoside. Because in vitro selection experiments require amplification of modified oligonucleotides, and because this amplification is normally done using a polymerase obtained from Nature, the most useful modifications are placed at positions in the oligonucleotide where modification is known to be tolerated by polymerases. On the nucleobase, these modifications either the sugar or the nucleobase. On the sugar, modification is preferred at the 2'-position, preferably 2'-deoxy-2'-amino nucleosides, or where functional groups are appended to the 2'-oxygen of a ribonucleoside in the biopolymer or in a ribonucleoside triphosphate. On the nucleobase, the modification are preferably appendages on the 5-position of pyrimidines, the 7-position of a 7-deazapurine, the 6-position exocyclic substitution (normally an amino group), or less preferably at the 2-position exocyclic substitution (normally an amino group). In non-standard nucleobases where the heterocycle numbering system is different, these modifications are placed at the structurally analogous positions. U.S. Ser. No. 07/594,290 filed Oct. 9, 1990, now issued as U.S. Pat. No. 5,432,272, and its continuations-in-part of which this application is a continuation-in-part, as well as Ser. No. 08/094,363, disclosed and claimed a variety of these structures, including nucleoside analogs carring amino, carboxyl, hydroxyl, thiol, aryl, indole, and imidazole groups. Through manipulation of the side chain functionality using chemistry well known in the art, a large set of functionalized oligonucleotides can be prepared suitable as a starting point for in vitro selection.

These approaches for increasing the diversity of functions that might be obtained by in vitro selection are not mutually exclusive. That is, they can be used at the same time. Indeed, the greatest diversity of functionality can be obtained from an in vitro selection experiment involving libraries of oligonucleotide analogs can be gained if all three strategies are used simultaneously, that is, if the oligonucleotide analogs contain non-standard nucleobases, modified standard nucleobases, and if the in vitro selection experiment is done in the presence of cofactors. Indeed, as discussed below, simply adding functionalized standard nucleosides, modified either on the nucleobase or on the sugar, in the absence of non-standard nucleobases as part of an expanded genetic alphabet, can lead to overfunctionalization.

U.S. Ser. No. 07/594,290, now issued as U.S. Pat. No. 5,432,272, outlined the structural features of the Watson-Crick base pair that serves as the basis for the amplification of nucleic acids by enzymes such as DNA and RNA polymerase and in the polymerase chain reaction (PCR). The disclosure also noted that nucleobases to which are appended moieties containing functional groups can provide oligonucleotide analogs that have properties that are not readily accessible, or perhaps not accessible at all, in natural oligonucleotides. For example, the disclosure pointed out that a single oligonucleotide sequences containing a T to which is appended as side chain bearing a biotin residue can first bind to a complementary oligonucleotide and the hybrid can then be isolated by virtue of the specific affinity of biotin to avidin (Langer, P. R., Waldrop, A. A., Ward, D. C. (1981) *Proc. Nat. Acad. Sci.* 78, 6633–6637). The latter is not a property readily available to a natural oligonucleotide. Further, it was stated that such modified natural nucleosides, as triphosphates, could serve as substrates for DNA and RNA polymerases, and be incorporated enzymatically into an oligonucleotide.

Not found in the prior art is a disclosure that functionalization of natural nucleobases can increase the likelihood that an oligonucleotide with a selectable property can be found in a pool of oligonucleotide derivatives of random sequence. U.S. Ser. No. 07/594,290, issued as U.S. Pat. No. 5,432,272 pointed this out in specific cases, and U.S. Ser. No. 08/375,132 (pending) amplified this point for the general case. U.S. Ser. No. 08/375,132 pointed out that libraries of oligonucleotide analogs built from a combination of natural nucleotides, natural nucleotides bearing functionalized side chains, or nucleotide building units bearing nucleobases with one of the non-standard hydrogen bonding patterns, would be useful in in vitro selection experiments. U.S. Ser. No. 08/094,363 disclosed specific modified standard nucleobases that would be useful for this purpose, in particular, to expand the catalytic power of oligonucleotides.

This invention is preferably characterized as an improvement on standard methods for performing in vitro selection, not obvious from the prior art covering in vitro selection performed with only standard, unmodified nucleotides. The improvement constitutes incorporating into the procedure for synthesizing a library one or more building units that carry functionalized standard nucleobases, or non-standard nucleobases, or both, to create libraries that contain (in the first case) "modified oligonucleotides" (to indicate that they differ from natural oligonucleotides in their appended moieties, but not in the pattern of hydrogen bonding), or (in the second case) "non-standard oligonucleotides" (to indicate that they differ from natural oligonucleotides in their pattern of hydrogen bonding, at least in part). Collectively, we refer to modified oligonucleotides and non-standard oligonucleotides as oligonucleotide analogs, distinct from conventional (or natural, or unmodified) oligonucleotides. Alternatively, the in vitro selection can start with oligonucleotide libraries composed entirely of conventional oligonucleotides, but where cofactors designed to contribute functionality to the oligonucleotides in the library via covalent binding.

While virtually any functionality can be incorporated into a nucleotide building block, standard or non-standard, both experiment and theory show that certain modifications are more useful than others. The most useful modifications carry functionality not found in natural oligonucleotides, including general acids and general bases with pKa values near 7, positively charged side chains, and aliphatic hydrophobic moieties. Therefore, in the preferred embodiment of the instant invention, certain constraints are desirable.

First, the nucleotide building block analogs that are incorporated into the oligonucleotide analogs that are the components of the library, once incorporated in the oligonucleotide, should not prevent said oligonucleotide from serving as a template for a polymerase. Further, in the case of non-standard nucleotide building blocks, the non-standard nucleobase and its complement must both be able to serve in both the template and as a triphosphate in a polymerase-based amplification system. Last, for both standard and non-standard oligonucleotides, it is convenient (but not necessary) for subsequent rounds of selection if the nucleoside analog triphosphate can also serve as a substrate in the final step of the amplification, the step that generates the new pool of oligonucleotides for in vitro selection.

U.S. Ser. No. 07/594,290, now issued as U.S. Pat. No. 5,432,272, discloses methods for achieving such amplifications with non-standard nucleobases, where the most preferred non-standard pyrimidine analog is 3-β-D-ribofuranosyl-(2,6-diaminopyrimidine), or its 2'-deoxyribose analog. The presently preferred complementary purine is xanthosine, or its 2'-deoxyribose analog.

Since U.S. Ser. No. 07/594,290 was filed, continued experimental work has increased the number of embodiments of the method claimed, and the compositions of matter that can be prepared using the method. These are disclosed in U.S. Ser. No. 08/375,132. An even wider range of polymerases has been shown to incorporate non-standard base pairs into duplex oligonucleotides, including the reverse transcriptase from human immunodeficiency virus 1, especially this polymerase with the smaller subunit removed, and the thermostable polymerases from *Thermotoga maritima, Pyrodictium abyssi,* and *Pyrodictium occultum.* The py(ADD) base in its pyrazine form has been incorporated into an oligonucleotide using T4 RNA ligase (J. J. Vögel, S. A. Benner (1994) *J. Am. Chem. Soc.* 116, 6929–6930), which is incorporated herein by reference.

Further, since U.S. Ser. No. 07/594,290 was filed, continued experimental work has also increased the number of routes available for the preparation of non-standard bases as components of oligonucleotides. (J. J. Vögel, M. M. Altorfer, S. A. Benner. *Helv. Chim Acta* 76, 2061–2069 (1993); Vögel, J. J., Benner, S. A. *Helv. Chim. Acta* 79, 1881–1898 (1996); Vögel, J. J., Benner, S. A. *Helv. Chim. Acata* 79, 1863–1880 (1996)). Additional information has been gathered concerning the properties of the non-standard heterocyclic systems. J. J. Vögel, U. von Krosigk and S. A. Benner. *J. Org. Chem.* 58, 7542–7547 (1993), and further heterocyclic ring systems have bee defined that implement the non-standard hydrogen bonding patterns disclosed in U.S. Ser. No. 07/594,290. Further, functional groups Z have been found to be preferred when the attachment to carbon is via an acetylenic linkage, as disclosed in Hobbs, Jr., F. W. (1989) (*J. Org. Chem.* 54, 3420–3422). The py(DDA) and py(ADD) implementations have been found to be most preferably implemented on carbocyclic analogs of ribose and deoxyribose rings.

When the improvement involves incorporation of a modified standard nucleotide, the requirements for interaction with polymerases are less stringent. During the amplification cycles, the modification need not be present in the standard nucleobase, permitting the amplification to proceed as in a classical in vitro selection experiment. However, in the first copying in the amplification, the modified nucleotide must be able to serve as a template. Further, while not necessarry to identify the amplified sequences, it is desirable for subbsequent rounds of selection if the modified nucleotide can be incorporated into the new library in the final polymerase cycle, and that the triphosphate of the modified nucleoside be acceptable at least to some extent. As noted in U.S. Ser. No. 07/594,290, now issued as U.S. Pat. No. 5,432,272, pyrimidines carrying appendages at the 5-position are accepted by many polymerases. Experiments in the inventor's laboratory now have shown that these pyrimidines also serve as templates for polymerization catalyzed by the Klenow fragment of DNA polymerase I from *E. coli*. Thus, the presently preferred embodiment of the instant invention that introduces functionality on standard nucleobases, does so by modifications of 2'-deoxyuridine and 2'-deoxycytidine at the 5-position of the pyrimidine ring, uses the Klenow fragment or one of its homologs as the polymerase for the initial and final rounds of amplification, and uses non-functional nucleoside triphosphates in intermediate rounds of amplification. Likewise, adenosine triphosphate derivatives carring appendages on the 6-position exocyclic amino group are also substrates for certain polymerases, such as T7 RNA polymerase (Folsom, V., Hunkeler, M. J., Haces, A., Harding, J. D. (1989) *Anal. Biochem.* 182, 309–314).

The improvement involving adding a functionalized cofactor to the library is the least demanding on the polymerase. The presently preferred cofactors are short oligoribonucleotides of defined sequence, preferably 4–6 nucleobases in length, whose 2',3'-diol end has been cleaved by periodate following a procedure well known in the art, and the resulting dialdehyde reacted with a functionalized amine in the presence of sodium cyanoborohydride to give a morphilo derivative carrying a fucntionality at the 3'-end. The presently most preferred amine is histamine.

As is well known in the art, in vitro selection may be used to generate catalysts as well as ligands. Methods for the selection of oligonucleotides that have a preselected catalytic activity from a library of oligonucleotides having a region of randomized sequence are well developed in the published literature (see Ekland, E. H., Bartel, D. P. (1996) *Nature* 382, 373–376, and references therein). Briefly, selection for catalytic oligonucleotides requires that the reaction catalyzed transform the structure of the catalytic oligonucleotides in a way that either allows them to be partitioned from the non-catalytic oligonucleotides, or allows them to be amplified in preference to the non-catalytic oligonucleotides. To the first end, the catalytic reaction may affix a biotin covalently to the catalytic oligonucleotides, allowing them to be partitioned from the non-catalytic oligonucleotides using an aviding affinity column. To the second end, the catalytic transformation may join a primer binding site to one end of the catalytically active oligonucleotides, allowing them to be preferentially amplified in a PCR. The improvement of the instant invention comprises including non-standard nucleobases into the oligonucleotides in the library, or including functionalized nucleobases into the library, or adding functionalized cofactors into the in vitro selection mixture. Selection for catalysts is especially well suited for the cofactor strategy, as the cofactor can be added to the selected oligonucleotide in a situation where the catalystic activity has practical application.

The introduction of nucleotide analogs into an oligonucleotide nearly always expands the conformational versatility and range of reactivity of the oligonucleotide analog when compared with the unmodified or fully standard oligonucleotide. This implies that the oligonucleotide analog essentially always has a higher probability of having a preselected behavior. As a corollary, this implies that a library comprised of oligonucleotide analogs will contain more individual oligonucleotides with the preselected behavior than the corresponding library built entirely from natural oligonucleotides.

However, overfunctionalization can generate oligonucleotides that no longer behave well, as discussed in U.S. Ser. No. 07/594,290, now issued as U.S. Pat. No. 5,432,272. For example, introducing hydrophobic moieties into a large fraction of the nucleobases in an oligonucleotide can decrease the solubility of the oligonucleotide, causing aggregation and precipitation. Further, introducing multiple functionality into an oligonucleotide can create undesired catalytic powers, most significantly ribonucleolytic activity that destroys the library. For these reasons, the preferred embodiment has less than 15% of the nucleotide units containing functionality. U.S. Ser. No. 07/594,290 disclosed that non-standard nucleobases permit the best control over the level of functionalization present in an oligonucleotide. When using functionalized standard nucleobases, the preferred embodiment introduces a single nucleobase (C, for example) only in modified form. The fraction of C in the oligonucleotide library is less than 15%, while the fraction of the other nucleotides is correspondingly higher, in the presently preferred embodiment.

Further, the presently preferred embodiment constructs libraries based on oligo-2'-deoxyribonucleotide analogs, as these are more stable to hydrolytic cleavage than oligoribonucleotide analogs.

Preferably the oligonucleotide analogs that form the components of a library of oligonucleotide analogs are from 20 to 300 nucleotides in length. These are most preferably prepared using terminal transferase to catalyze the elongation of a "primer" of defined sequence in the presence of nucleoside triphosphates and nucleoside triphosphate analogs. The ratio of triphosphate molecules to primer molecules determines the average length of the oligonucleotides in the library. This average length is assessed by agarose gel electrophoresis with ethidium bromide used as a visualizing agent. The ratio of building blocks in the library is determined by the ratio of triphosphates in the incubation mixture with terminal transferase. To assess the overall composition of the pool, a sample of the mixture is treated with deoxyribonuclease, the nucleotide products dephosphorylated using alkaline phosphatase, and the nucleoside products resolved and quantitated by high performance liquid chromatography.

Cofactors can be used in many different ways in an in vitro selection experiment. In the most general sense, a cofactor is anything that contributes to the functioning of the oligonucleotide is not encoded in the sequence of the oligonucleotide or the oligonucleotide analog. In this very general sense, the divalent cation (e.g. magnesium) present in many in vitro selection experiments is a cofactor. It permits oligonucleotides to adopt conformations that are important for function as a ligand, receptor, or catalyst, and may also contribute reactivity that is essential to the catalytic behavior of the oligonucleotide or oligonucleotide analog.

Cofactors that are the objects of the instant invention can be more narrowly defined. First, the instant invention includes only those cofactors that present organic functionality to the library, that is, those whether the functional group is constructed from the elements carbon, hydrogen, nitrogen, oxygen, halogen, sulfur and phosphorus. The preferred functional groups are amine, guanidinium, hydroxyl, carboxylate, thiol, and heterocycles. In this contest, aliphatic hydrophobic appendages are also regarded as "functional" (even though they contain no functional groups), because they confer upon an oligonucleotide a property (aliphatic hydrophobicity) that is not found in conventional oligonucleotides. Most preferably is functionality important for catalysis, specifically imidazole, as disclosed in U.S. Ser. No. 08/094,363, functionality that contributes cationic groups, specifically amines and guanidiniums, and functionality that permits the cofactor to adopt unusual three dimensional conformations, specifically thiols. Several of these functional groups are found in the modified nucleobases disclosed herein. They can also be provided by cofactors.

Next, we consider cofactors of five classes based on their potential for interacting with an oligonucleotide. The first interact primarily through coulombic interactions between a positively charged cofactor and the anionic phosphate backbone of an oligonucleotide. The polyamines spermine and spermidine are examples of cofactors of this class. The interaction between a polycationic cofactor and an oligonucleotide can be supplemented by secondary actions that confer specificity to the binding, that is, that causes this class of cofactor to bind preferentially to one segment of an oligonucleotide chain over another. This specificity in binding can be selected in the in vitro selection experiment.

The second class interacts with an oligonucleotide by intercalation. Again, the specificity of binding is low.

The third class of cofactor interacts with an oligonucleotide by interacting with the nucleobases in a non-intercalative sense, and also in a non-Watson-Crick sense. Netropsin is an example (Zimmer, C. (1975) *Prog. Nucleic Acid Res. Mol. Biol.* 15, 285–318). The specificity of binding is determined by the sequence of the oligonucleotide, in particular, how that sequence places hydrogen bond donating and accepting groups into the major and minor grooves.

A fourth class of cofactor interacts with an oligonucleotide primarily through formation of Watson-Crick base pairs, with Watson-Crick specificity being the primary basis for selectivity of binding. The presently preferred cofactors of this class are short oligonucleotides between 2 and 10 nucleotides in length to which is appended functionality. The most preferred cofactors are generated by treating ribonucleotide meeting this description with sodium periodate, condensing the resulting 2',3'-seco dialdehyde with a primary amine carrying additional functionality, and reducing the adduct to yield a morphilino analog of the 3'-terminal ribonucleoside following the procedures of Khym (Khym, J. X. (1963) *Biochemistry* 2, 344), Brown & Read (Brown, D. M., Reed, A. P. (1965) *J. Chem. Soc.* 1965, 5072) and Stirchak et al. (Stirchak, E. P., Summerton, J. E.., Weller, D. D. (1989) *Nucleic Acids Res.* 17, 6129–6141). The preferred primary amines are short polypeptides from two to six amino acids in length, with the residues in the peptide selected from the group consisting of the 20 proteinogenic amino acids excluding lysine. These can be prepared by automated solid phase synthesis by procedures well known in the art.

The fifth class of cofactor interacts with an oligonucleotide or an oligonucleotide analog through the formation of a covalent bond. The presently preferred mode of interaction is a covalent bond between the cofactor and the functional group of a functionalized nucleobase. For example, a library of oligonucleotide analogs incorporating one or more mercaptopropargyl side chains is subjected to an in vitro selection experiment for catalysis in an acetate-borate buffer at pH 8.0. To this incubation mixture is added one or more functionalized thiols as mixed disulfides with 4-nitrothiosalicylic acid in a 1.5 fold excess. The mixture undergoes disulfide exchange rapidly under these conditions, yielding oligonucleotide analogs to which are appended functional groups via a disulfide bond. The presently preferred cofactors are short polypeptides from two to six amino acids in length, each peptide carrying exactly one cysteine residue, with the remainder of the residues in the peptide selected from the group consisting of the proteinogenic amino acids excluding cysteine. These can be prepared by automated solid phase synthesis by procedures well known in the art.

As another example, a library of oligonucleotide analogs incorporating one or more aminopropargyl side chains is subjected to an in vitro selection experiment for catalysis in an acetate buffer at pH 6.0. To this incubation mixture is added one or more functionalized aldehydes. The aldehyde rapidly forms an imine with the amino group of the side chain, yielding oligonucleotide analogs to which are appended functional groups via a C=N bond. The presently preferred cofactors are prepared from short peptides from two to six amino acids in length, each peptide having an N-terminal serine, with the remainder of the residues in the peptide selected from the group consisting of the proteinogenic amino acids excluding lysine. These can be prepared by automated solid phase synthesis by procedures well known in the art. When such peptides are treated in aqueous solution with sodium periodate, the N-terminal serine is converted to a terminal glyoxylic acid residue.

EXPERIMENTAL

EXAMPLE 1

Synthesis of Derivatives of Uridine and 2'-Deoxyuridine Suitable for Incorporation into an Oligonucleotide Library.

N-propargyltrifluoroacetamide

This compound has been prepared using a literature method (K. A. Cruickshank, D. L. Stockwell (1988) *Tetrahedron Lett.* 29, 5221). Propargylamine (90.9 mmol, 5 g, 6.227 mL) was added to methanol (90 mL) and the solution cooled to 0° C. Ethyl trifluoroacetate (1.3 equiv., 118.2 mmol, 16.8 g, 14.1 mL) was added and the mixture stirred at room temperature for 24 h. The solvent was evaporated, the residue diluted with 90 mL chloroform and washed with aqueous NaHCO$_3$ solution (2×75 mL) and water (1×75 mL). The organic layer was evaporated and the orange residue distilled in vacuum to give N-propargyltrifluoroacetamide (13.171 g, 96%) as a colorless liquid which solidifies at −20° C. bp: 41° C./1.5 mm (bp ref.: 51° C./2.5 mm), mp: 31–33° C. $^1$H-NMR (CDCl$_3$): 2.34 (m, 1H, CH), 4.15 (dd, 2H, CH$_2$), 7.80 (br s, H, NH). $^1$H-NMR (CDCl$_3$): 2.34 (t, 1H), 4.16 (dd, 2H), 7.00 (br s, 1H). $^{13}$C-NMR (CDCl$_3$): 29.4 (CH$_2$), 72.4 (CH), 77.0 (C), 109.859, 113.673, 117.470, 121.276 (CF$_3$, J=286.37 Hz), 156.748, 157.249, 157.750, 158.250 (CO, J=37.77 Hz).

5-(3-Trifluoroacetamidopropyn-1-yl)-2'-deoxyuridine

The strategy to prepare 5-position substituted nucleobases involves coupling a 5-iodonucleobase derivative with an acetylene derivative using either a Pd(II) catalyst (e.g. (Ph$_3$P)$_2$PdCl$_2$, M. J. Robins and P. J. Barr, *J. Org. Chem.* 48, 1854 (1983) for the 5'-DMT-protected uridine derivative (see also J. Haralambidis, M. Chai, and G. W. Tregear, *Nucl. Acids Res.* 15, 4857 (1987); K. J. Gibson and S. J. Benkovic, *Nucl. Acids Res.* 15, 6455 (1987))), or a Pd(0) catalyst (e.g. (Ph$_3$P)$_4$Pd) (M. J. Robins, R. S. Vinayak, and S. G. Wood, *Tetrahedron Lett.* 31, 3731 (1990)). The use of Pd(0) requires shorter reaction times and gives purer products in better yields. Anaogous recipes for preparing analogous-compounds can be found in (G. T. Crisp and B. L. Flynn, *J. Org. Chem.* 58, 6614 (1993).).

5-(3-Trifluoroacetamidopropyn-1-yl)-2'-deoxyuridine is mentioned in the literature (A. L. Casalnuovo and J. C. Calabrese, *J. Am. Chem. Soc.* 112, 4324 (1990). F. W. Hobbs, Jr., *J. Org. Chem.* 54, 3420 (1989)), although without complete synthesis recipe or spectroscopic data. 5-Iodo-2'-deoxyuridine (1.4 mmol, 500 mg) was dissolved in dry dimethylformamide (DMF, 12 mL) and Ar was bubbled through this solution for 10 min. Then, (Ph$_3$P)$_4$Pd (0.1 equiv., 0.141 mmol, 163 mg) was added and Ar was bubbled through the solution for another 5 min. Triethylamine (2.0 equiv., 2.8 mmol, 285 mg, 0.393 mL) was added via syringe followed by addition of N-propargyltrifluoroacetamide (2.5 equiv., 3.53 mmol, 533 mg and CuI (0.2 equiv., 0.282 mmol, 53.7 mg). The mixture was stirred at 40° C. for 5 h, the solvent was evaporated, and the residue dissolved in MeOH/methylene chloride 1:1 (10 mL). Ion exchange resin (Bio-Rad AG1 X8, HCO$_3$-form, 1.5 g, prepared from the chloride form by eluting through a column with the 16 fold volume of 1 M NH$_4$HCO$_3$ solution followed by deionized water and finally with 0.5 M NH$_4$HCO$_3$ solution; no Cl$^-$ was detected) was added to remove the Et$_3$N.HI side product, and the mixture stirred at room temperature for 30 min. The mixture was passed through Celite, the solid washed with MeOH/methylene chloride 1:1 (10 mL) and the solvents removed by rotary evaporation. The residue was purified by column chromatography (chlorofornm/MeOH 8.25:1.75) to yield 5-(3-trifluoroacetamidopropyn-1-yl)-2'-deoxyuridine (ca. 95%) contaminated with some DMF. R$_f$: 0.42 (chloroform/MeOH 8.25:1.75). $^1$H-NMR (DMSO-d$_6$): 2.13 (m, 2H, 2'), 3.60 (m, 2H, 5'), 3.81 (m, 1H, 4'), 4.24 (m, 3H, H-9, 3'), 5.12 (t, 1H, 5'-OH), 5.27 (d, 1H, 3'-OH), 6.11 (t, 1H, 1'), 8.22 (s, 1H, H-6), 10.09 (t, 1H, NH chain), 11.67 (s, 1H, NH cylc.). $^{13}$C-NMR (DMSO-d6): 29.5 (C-9), 40.7 (2'), 61.0 (5'), 70.2 (3'), 75.4 (C-8), 84.8 (1'), 87.5, 87.7 (4', C-7), 97.7 (C-5), 113.9, 117.8 (q, CF$_3$, J=287.95 Hz), 144.2 (C-6), 149.5 (C-2), 155.9, 156.4 (q, COCF$_3$, J=37.25 Hz), 161.7 (C-4).

5-(3- Trifluoroacetamidopropyn-1-yl)-uridine

This compound was prepared similarly. 5-Iodouridine (1.35 mmol, 500 mg) was dissolved in dry DMF (12 mL) and Ar was bubbled through the solution for 10 min. Then, (Ph$_3$P)$_4$Pd (0.1 equiv., 0.1351 mmol, 156 mg) was added and Ar was bubbled through the solution for another 5 min. Triethylamine (2.0 equiv., 2.703 mmol, 273 mg, 0.376 mL) was added via syringe followed by addition of N-propargyltrifluoroacetamide (2.5 equiv., 3.38 mmol, 510 mg and CuI (0.2 equiv., 0.27 mmol, 51.5 mg). The mixture was stirred at 45° C. for 3.5 h, then the solvent was evaporated, and the residue dissolved in MeOH/methylene chloride 1:1 (10 mL). Ion exchange resin (Bio-Rad AG1 X8, HCO$_3$-form, 1.5 g) was added to remove Et$_3$N.HI, and the mixture stirred at room temperature for 20 min. The mixture was then filtered through Celite, the solid washed with MeOH/methylene chloride 1:1 (10 mL) and the solvents removed by rotary evaporation. The residue was purified by column chromatography (chloroform/MeOH 8.25:1.75) to yield 5-(3-trifluoroacetamidopropyn-1-yl)-uridine (ca. 95%) as a yellow foam contaminated with some Et$_3$N.HI. R$_f$:0.43 (chloroform/MeOH 8.25:1.75). $^1$H-NMR (DMSO-d6): 3.61 (m, 2H, 5'), 3.86 (m, 1H, 4'), 3.93–4.08 (m, 2H, 2', 3'), 4.23 (m, 2H, H-9), 5.08 (d, 1H, OH), 5.19 (t, 1H, OH), 5.41 (d, 1H, OH), 5.75 (d, 1H, 1'), 8.48 (s, 1H, H-6), 10.10 (t, 1H, NH chain), 11.64 (s, 1H, NH cycl.). $^{13}$C-NMR (DMSO-d6): 29.5 (C-9), 60.5 (5'), 69.6 (3'), 73.8 (2'), 75.3 (C-8), 85.0 (4'), 87.6, (C-7), 88.3 (1'), 97.8 (C-5), 113.9, 117.7 (q, CF$_3$, J=288.48 Hz), 144.4 (C-6), 149.7 (C-2), 155.9, 156.4 (q, COCF$_3$, J=36.80 Hz), 161.6 (C-4).

5-(3-Trifluoroacetamidopropyn-1-yl)-5'-O-dimethoxytrityl-2'-deoxy-uridine 5-(3-Trifluoroacetamidopropyn-1-yl)-2'-deoxyuridine (1.34 mmol, 506 mg) was coevaporated with pyridine, then dissolved in dry pyridine (10 mL) and cooled to 0° C. Et$_3$N (2 equiv., 2.684 mmol, 271 mg, 0.373 mL), dimethylaminopyridine (DMAP, 0.25 equiv., 0.3355 mol, 41 mg) and dimethoxytrityl chloride (DMTCl, 1.2 equiv., 1.61 mmol, 545.1 mg) were added and the mixture stirred at 0° C. for 5 min. and at room temperature for 4 h. Thin layer chromatography (tlc, chloroform/10% MeOH, R$_f$=0.47) showed that all starting material had been consumed. MeOH (2 mL) was added and the solvents removed by rotary evaporation. The residue was partitioned (EtOAc/aqueous NaHCO$_3$ solution), the combined organic layers washed with water, dried (Na$_2$SO$_4$) and the solvent evaporated. The residue was purified by column chromatography (chloroform/10% MeOH) to give 5-(3-trifluoroacetamidopropyn-1-yl)-5'-O-dimethoxytrityl-2'-deoxyuridine (902 mg, 99%) as a yellow foam. $^1$H-NMR (CDCl$_3$): 2.44–2.61 (m, 2H, 2'), 3.34 (m, 2H, 5'), 3.73 (s, 6H, MeO), 3.89 (m, 1H, 4'), 4.14 (m, 2H, H-9), 4.59 (m, 1H, 3'), 6.34 (t, 1H, 1'), 6.80 (m, 4H, DMT), 7.14–7.33, 7.61–7.70 (m, 9H, DMT), 8.21 (s, 1H, H-6). $^{13}$C-NMR (CDCl$_3$): 30.3 (C-9), 41.6 (2'), 55.2 (MeO), 63.5 (5'), 72.0 (3'), 75.3 (C-8), 86.0 (1'), 86.9 (Cq trityl), 87.0, (C-7), 87.3 (4'), 99.9 (C-5), 113.3 (DMT), 113.8, 117.6 (q, CF$_3$, J=286.52 Hz), 126.9, 127.8, 128.0, 129.9, 135.4 (all DMT), 143.6 (C-6), 144.5 (DMT), 149.4 (C-2), 156.4, 156.9 (q, COCF$_3$, J=37.70 Hz), 158.5 (DMT), 162.6 (C-4).

5-(3-Trifluoroacetamidopropyn-1-yl)-5'-O-dimethoxytrityluridine 5-(3-Trifluoroacetamidopropyn-1-yl)-uridine (1.272 mmol, 500 mg) was coevaporated with pyridine, then dissolved in dry pyridine (10 mL) and cooled to 0° C. Et$_3$N (2 equiv., 2.544 mmol, 257 mg, 0.354 mL), DMAP (0.25 equiv., 0.318 mol, 38.8 mg) and DMTCl (1.2 equiv., 1.526 mmol, 516.7 mg) were added and the mixture stirred at 0° C. for 5 min. and at room temperature for 5 h. Analysis by tlc (chloroform/10% MeOH, R$_f$=0.33) did not show any starting material remaining. MeOH (2 mL) was added and the mixture evaporated. The residue was extracted (ethyl acetate/aqueous NaHCO$_3$ solution), the combined organic layers washed with water, dried (Na$_2$SO$_4$) and the solvent evaporated. The residue was purified by column chromatography (chloroform/10% MeOH) to give 286 mg (32%) 5-(3-trifluoroacetamidopropyn-1-yl)-5'-O-dimethoxytrityluridine as a yellow foam. $^1$H-NMR (CDCl$_3$): 3.32–3.41 (m, 2H, 5'), 3.70 (s, 6H, MeO), 3.80–3.88 (m, 1H, 4'), 4.19 (m, 2H, H-9), 4.35–4.44 (m, 2H, 2', 3'), 5.91 (m, 1H, 1'), 6.79 (d, 4H, DMT), 7.19–7.71 (m, 9H, DMT), 8.18 (s, 1H, H-6). $^{13}$C-NMR (CDCl$_3$): 30.2 (C-9), 55.2 (MeO), 62.7 (5'), 70.5 (3'), 74.9 (2'), 75.5 (C-8), 84.3 (4'), 86.9 (Cq trityl), 87.6, (C-7), 90.0 (1'), 99.1 (C-5), 113.3 (DMT), 113.6, 117.4 (q, CF$_3$, J=286.90 Hz), 126.9, 127.8, 128.0, 129.9, 135.4 (all DMT), 143.6 (C-6), 144.4 (DMT), 149.2 (C-2), 156.4, 157.0 (q, COCF$_3$, J=38.23 Hz), 158.5 (DMT), 162.7 (C-4).

3'-O-Acetyl-5-(3-trifluoroacetamidopropyn-1-yl)-5'-O-dimethoxytrityl-2'-deoxyuridine 5-(3-Trifluoroacetamidopropyn-1-yl)-5'-O-dimethoxytrityl-2'-deoxyuridine (1.328 mmol, 902 mg) was coevaporated with pyridine and then dissolved in pyridine (10 mL) and DMAP (0.25 equiv., 0.332 mmol, 40.5 mg), Et$_3$N (2.5 equiv., 3.32 mmol, 335 mg, 0.462 mL) and Ac$_2$O (1.2 equiv., 1.594 mmol, 162.5 mg, 0.15 mL) were added. The mixture was stirred at room temperature for 2.5 h (TLC, chloroform/10% MeOH, R$_f$=0.75). MeOH (5 mL) was added to stop the reaction and the solvents were removed by rotary evaporation. The residue was extracted (water/ethyl acetate), the organic layer dried (Na$_2$SO$_4$) and the solvent evaporated. The residue was purified by column chromatography (chloroform/10% MeOH) to give 3'-O-acetyl-5-(3-trifluoroacetamidopropyn-1-yl)-5'-O-dimethoxytrityl-2'-deoxyuridine (937 mg, 98%) as a yellow foam. $^1$H-NMR (CDCl$_3$): 2.08 (s, 3H, Ac), 2.38–2.64 (m, 2H, 2'), 3.42 (m, 2H, 5'), 3.77 (s, 6H, MeO), 3.96 (m, 1H, 4'), 4.18 (m, 2H, H-9), 5.45 (m, 1H, 3'), 6.34 (t, 1H, 1'), 6.85 (m, 4H, DMT), 7.23–7.48, 7.63–7.71 (m, 9H, DMT), 8.20 (s, 1H, H-6). $^{13}$C-NMR (CDCl$_3$): 20.8 (Ac), 30.2 (C-9), 38.7 (2'), 55.1 (MeO), 63.5 (5'), 74.9 (3'), 75.1 (C-8), 84.4 (1'), 85.3 (4'), 87.1 (Cq trityl), 87.2 (C-7), 99.4 (C-5), 113.3 (DMT), 113.6, 117.4 (q, CF$_3$, J=287.42 Hz), 126.9, 127.7, 128.0, 129.9, 135.2 (all DMT), 143.1 (C-6), 144.3 (DMT), 149.4 (C-2), 156.3, 156.8 (q, COCF$_3$, J=37.78 Hz), 158.6 (DMT), 162.0 (C-4), 170.3 (Ac).

2',3'-Di-O-acetyl-5-(3-trifluoroacetamidopropyn-1-yl)-5'-O-dimethoxy-trityluridine 5-(3-Trifluoroacetamidopropyn-1-yl)-5'-O-dimethoxytrityluridine (0.4115 mmol, 286 mg) was coevaporated with pyridine and then dissolved in pyridine (10 mL) and DMAP (0.5 equiv., 0.206 mmol, 25 mg), Et$_3$N (5 equiv., 2.058 mmol, 208 mg, 0.886 mL) and Ac$_2$O (2.4 equiv., 0.988 mmol, 100.68 mg, 0.093 mL) were added. The mixture was stirred at room temperature for 1 h (TLC: chloroform/10% MeOH, R$_f$=0.77), then MeOH (5 mL) was added to stop the reaction and it was evaporated to dryness. The residue was extracted (water/ethyl acetate), the organic layer dried (Na$_2$SO$_4$) and the solvent evaporated. The residue was purified by column chromatography (chloroform/10% MeOH) to give 2',3'-di-O-acetyl-5-(3-trifluoroacetamidopropyn-1-yl)-5'-O-dimethoxy-trityluridine (285 mg, 89%) as a yellow foam. $^1$H-NMR (CDCl$_3$): 2.15 (s, 3H, Ac), 2.17 (s, 3H, Ac), 3.41–3.56 (m, 2H, 5'), 3.82 (s, 6H, MeO), 3.95–4.05 (m, 1H, 4'), 4.31 (d, 2H, H-9), 5.65–5.68, 5.76–5.81 (m+m, 2H, 2', 3'), 6.29 (d, 1H, 1'), 6.90 (d, 4H, DMT), 7.32–7.44, 7.72–7.79 (m, 9H, DMT), 8.18 (s, 1H, H-6). $^{13}$C-NMR (CDCl$_3$): 20.3, 20.4 (2×Ac), 30.1 (C-9), 55.1 (MeO), 62.7 (5'), 71.2 (3'), 73.0 (2'), 74.7 (C-8), 82.3 (4'), 85.6 (1'), 87.2 (Cq trityl), 87.4 (C-7), 99.9 (C-5), 113.3 (DMT), 109.8, 113.6, 117.4, 121.2 (q, CF$_3$, J=287.50 Hz), 126.9, 127.8, 128.0, 129.8, 134.8, 136.5 (all DMT), 142.9 (C-6), 143.9 (DMT), 148.8 (C-2), 155.8, 156.3, 156.8, 157.3 (q, COCF$_3$, J=37.25 Hz), 158.5 (DMT), 161.9 (C-4), 169.7 (Ac).

3'-O-Acetyl-5-(3-trifluoroacetamidopropyn-1-yl)-2'-deoxyuridine

3'-O-Acetyl-5-(3-trifluoroacetamidopropyn-1-yl)-5'-O-dimethoxytrityl-2'-deoxyuridine (1.30 mmol, 937 mg) was dissolved in dry MeOH (1 mL). A solution of anhydrous HCl in anhydrous MeOH (10%, 1 mL) was added. TLC showed that the reaction was completed after 3 min. (TLC, chloroform/10% MeOH, R$_f$=0.46). The mixture was cooled to 0° C. and aqueous NaHCO$_3$ solution was added to adjust pH 7. The mixture was extracted (ethyl acetate), the organic phase separated and dried (Na$_2$SO$_4$), and the solvents removed by rotary evaporation. The residue was purified by column chromatography (chloroform/10% MeOH) to give 3'-O-acetyl-5-(3-trifluoroacetamidopropyn-1-yl)-2'deoxyuridine (371 mg, 68%) as a slightly yellow foam. $^1$H-NMR (CD$_3$OD): 2.03 (s, 3H, Ac), 2.18–2.40 (m, 2H, 2'), 3.71 (m, 2H, 5'), 4.02 (m, 1H, 4'), 4.19 (d, 2H, H-9), 5.21 (m, 1H, 3'), 6.14 (t, 1H, 1'), 8.25 (s, 1H, H-6). $^{13}$C-NMR (CD$_3$OD): 20.9 (Ac), 30.7 (C-9), 39.0 (2'), 62.8 (5'), 76.0 (3'), 76.4 (C-8), 86.9 (1'), 87.1 (C-7), 88.5 (4'), 99.9 (C-5), 111.6, 115.4, 119.2, 123.0 (q, CF$_3$, J=285.99 Hz), 145.5 (C-6), 151.1 (C-2), 158.2, 158.7 (q, COCF$_3$, J=37.78 Hz), 164.4 (C-4), 172.2 (Ac). Fab$^+$-MS: 420.1026 ((M+1)$^+$)

2',3'-Di-O-Acetyl-5-(3-trifluoroacetamidopropyn-1-yl)-uridine

2',3'-Di-O-acetyl-5-(3-trifluoroacetamidopropyn-1-yl)-5'-O-dimethoxy-trityluridine (0.366 mmol, 285 mg) was dissolved in dry MeOH (1 mL). A solution of anhydrous HCl in anhydrous MeOH (10%, 1 mL) was added at 0° C. and the reaction was completed after 5 min. (TLC, chloroform/10% MeOH, R$_f$=0.32). Aqueous NaHCO$_3$ solution was added to adjust pH 7 at 0° C. The aqueous phase was extracted (ethyl acetate), the organic phase separated and dried (Na$_2$SO$_4$), and the solvent evaporated. The residue was purified by column chromatography (chloroform/10% MeOH) to give 2',3'-di-O-acetyl-5-(3-trifluoroacetamidopropyn-1-yl)-uridine (144 mg, 82.5%) as a slightly yellow foam. $^1$H-NMR (CDCl$_3$): 2.06 (s, 3H, Ac), 2.11 (s, 3H, Ac), 3.82–4.01 (m, 2H, 5'), 4.21 (m, 1H, 4'), 4.28 (m, 2H, H-9), 5.44 (m, 2H, 2',3'), 6.04 (d, 1H, 1'), 8.16 (s, 1H, H-6). $^{13}$C-NMR (CDCl$_3$): 20.2, 20.4 (2×Ac); 30.3 (C-9), 61.1 (5'), 70.6 (3'), 73.4 (2'), 74.8 (C-8), 83.4 (4'), 87.6 (1'), 87.9 (C-7), 99.2 (C-5), 110.0, 113.8, 117.6, 121.4 (q, CF$_3$, J=287.42 Hz), 144.4 (C-6), 149.5 (C-2), 156.6, 157.0, 157.5, 158.0 (q, COCF$_3$, J=37.25 Hz), 162.5 (C-4), 170.1, 170.2 (2×Ac).

5-(3-aminopropyn-1-yl)-2'-deoxyuridine triphosphate

Triphosphates were synthesized by the method of Ludwig and Eckstein (J. Ludwig and F. Eckstein (1989) *J. Org. Chem.* 54, 631). 3'-O-Acetyl-5-(3-trifluoroacetamidopropyn-1-yl)-2'-deoxyuridine (0.1 mmol, 41.9 mg) was coevaporated with pyridine and dissolved in dry pyridine (0.1 mL)/dry 1,4-dioxane (0.3 mL). 2-Chloro-4H-1,3,2-benzodioxaphosphorin-4-one (1.1 equiv., 0.11 mL 1 M solution) was added. A precipitate was formed and the mixture was stirred for 10 min. Then, tributylammonium pyrophosphate (70 mg) in dry DMF (0.35 mL)/tributylamine (0.1 mL) was added, giving a clear solution which was stirred for 10 min. An 1% solution of iodine in pyridine/water 98:2 (2.2 mL) was added and the immediately decolorized solution was stirred for another 15 min. After addition of a few drops of a 5% Na$_2$SO$_3$ solution it was evaporated at room temperature, the residue taken up in water (5 mL) and stirred at room temperature for 30 min. Then, concentrated aqueous ammonia (20 mL) was added and the mixture stirred at 50° C. for 4 h. The organic solvents were removed by rotary evaporation at room temperature and the residue purified by column chromatography (Sephadex DEAE cellulose, previously equilibrated with TEAB buffer) using a 0.2 M–0.6 M gradient of triethylammonium bicarbonate (TEAB) buffer solution. The UV active fractions were evaporated at room temperature to yield 5-(3-aminopropyn-1-yl)-2'-deoxyuridine triphosphate, contaminated with some diphosphate.

EXAMPLE 2

Synthesis of Derivatives of 2'-Deoxycytidine Suitable for Incorporation into an Oligonucleotide Library S-Propargyl thioacetate A solution of triphenylphosphine (2.142 g, 8.17 mmol) in anhydrous tetrahydrofuran (THF, 33 mL) was treated at 0° C. dropwise with diethylazodicarboxylate (DIAD, 1.608 mL, 8.17 mmol). A white precipitate was formed. The mixtue was stirred for 30 min, and a solution of CH$_3$COSH (622 mg, 0.584 mL, 8.17 mmol) and propargyl alcohol (0.317 mL, 5.44 mmol) in 20 mL anhyrous THF was added over a period of 20 min. The mixture was stirred for 2 h at 0° C. (a clear solution resulted) and then for another 4 h at room temperature (RT). Methanol (0.110 mL) was then added, and the solvents removed by rotary evaporation (50° C., 200 mbar). The residue (ca. 8 g of a yellow liquid) was stored at −20° C. for 12 h, during which most of the POPh3 crystallized. The liquid was removed by decantation, the crystals washed with petroleum ether (4 times), the liquid and washings were combined, and the solvents removed by rotary evaporation. The residue was chromatographed (silica, eluting first with petroleum ether, then with petroleum ether:ether 99.5:0.5) to yield the propargyl S-thioester of thioacetic acid (577 mg, 5.06 mmol, 93%) as a light yellow liquid.

S-Acetate of 5-(3-mercaptopropyn-1-yl)-2'-deoxycytidine

A solution of 5-iodo-2'-deoxycytidine (Sigma, 92 mg, 0.260 mmol) and Pd(PPh$_3$)$_4$ (30 mg, 0.026 mmol) in absolute DMF (1.3 mL) was treated sequentially with triethylamine (0.072 mL, 53 mg, 0.520 mmol), the propargyl S-thioester of thioacetic acid (74 mg, 0.650 mmol), and CuI (10 mg, 0.052 mmol). The mixture was stirred at RT (4 h), the solvents were removed in high vacuum, and the residue was chromatographed (silica, CH$_2$Cl$_2$:MeOH 9:1) to yield the S-acetate of 5-(3-mercaptopropyn-1-yl)-2'-deoxycytidine (77 mg, 0.227 mmol, 88%) as a light yellow oil.

The mixed disulfide between tert-butylthiol and 5-(3-mercaptopropyn-1-yl)-2'-deoxycytidine Under argon, a solution of (tBu)OCON(S-tBu)-NHCOOtBu (1.753 g, 5.470 mmol) in acetonitrile (18 mL) was treated with concentrated aqueous ammonia (29%). To this mixture was added the S-acetate of 5-(3-mercaptopropyn-1-yl)-2'-deoxycytidine (416 mg, 1.226 mmol) in a CH$_3$CN:H$_2$O mixture (9:1, total volume 40 mL) After 6.5 h, the pH of the reaction mixture was adjusted to 5 with aqueous HCl, and the solvents were removed by rotary evaporation. Chromatography of the residue yielded the mixed disulfide between tert-butylthiol and 5-(3-mercaptopropyn-1-yl)-2'-deoxycytidine (128 mg, 0.332 mmol, 27%).

The mixed disulfide between tert-butylthiol and 5-(3-mercaptopropyn-1-yl)-2'-deoxycytidine (128 mg, 0.332 mmol) in anhydrous DMF (2.6 mL) is treated dropwise with DMF-dimethylacetal (0.640 mL, 3.73 mL). After incubation for 1 h, the solvents were removed under high vacuum to yield the mixed disulfide between tert-butylthiol and 5-(3-mercaptopropyn-1-yl)-2'-deoxycytidine with the 4-amino group of the nucleobase protected as the dimethylformamide derivative.

This derivative is converted to the triphosphate of the modified cytidine nucleoside via the procedure described above for the 2'-deoxyuridine derivative.

EXAMPLE 3

Synthesis of Derivatives of 2'-Deoxyadenosine Suitable for Incorporation into an Oligonucleotide Library Solutions of O$^6$-phenyl-2'-deoxyinosine (Ferentz, A., Verdine, G. L. Nucleosides Nucleotides (1992) 11, 1749–1763) (each 1 mmol) in DMF-water (20 mL) are individually treated with the mxde disulfide between t-butyl thiol and cysteamine, hexylamine, phenethylamine, and the monotrifluoroacetamido derivative of ethylenediamine (1 M final concentration of each) to generate the corresponding 2'-deoxyadenosine derivatives. These are converted to the corresponding derivatives of 2'-deoxyadenosine carrying at the N(6) position the substituents —CH$_2$—CH$_2$—SS—C(CH$_3$)$_3$, (CH$_2$)$_5$CH$_3$, —CH$_2$CH$_2$-phenyl, and —CH$_2$CH$_2$NHCOCF$_3$, respectively. These are converted to the corresponding triphosphates following the procedure described above.

EXAMPLE 4

Library of Oligonucleotides Containing Functionalized Nucleobases

The oligonucleotide below containing a spacer (Seq1) and a 5'-primer binding site (5'PBS) was prepared.

5'-(Seq1)TTTTTCTAGAGA-(5'PBS)-3'

A solution containing approximately 60 nmol of these was then treated with terminal transferase, where a mixture of 2'-deoxynucleoside triphosphates (10 μM total) following the procedure in Maniatis et al. (*Molecular Cloning*, (1982) Cold Spring Harbor Laboratory, p. 148). The product was a library of oligonucleotides to which a randomized sequences (RanSeq) was appended with an average length of ca. 200 bases.

5'-(Seq1)TTTTTCTAGAGA-(5'PBS)-(RanSeq)-3'

After the pool of mixed triphosphates is consumed, 20 equivalents of TTP was added, and the polymerization is continued to affix an oligo-T tail to each of the supported oligonucleotides.

5'-(Seq1)TTTTTCTAGAGA-(5'PBS) (RanSeq)-(T)$_{20}$-3'

The library was then examined by agarose gel electrophoresis on agarose using ethidium bromide staining, which revealed a range of oligonucleotides with lengths of 100 to 200 bases. To assess the overall composition of the library, a sample of the mixture was treated with deoxyribonuclease, the nucleotide products dephosphorylated using alkaline phosphatase, and the nucleoside products resolved and quantitated by high performance liquid chromatography.

The library is then modified by repeating this procedure, but incorporating the triphosphate of 3-β-D-(2'-deoxyribofuranosyl)-(2,6-diaminopyrimidine) (5% by mole relative to the total of the triphosphates) and the triphosphate of 5-(3-aminopropyn-1-yl)-2'-deoxyuridine (5% by mole relative to the total of the triphosphates). Thus, the incubation mixture presented to the terminal transferase contains 60 nmol of 5'(Seq1) TTTTTCTAGAGA-(5'PBS)-3', 3-β-(2'-deoxyribofuranosyl)-(2,6-diaminopyrimidine) triphosphate (500 nmol), 5-(3-aminopropyn-1-yl)-2'-deoxyuridine triphosphate (500 nmol), ATP (3 μmol), GTP (3 μmol), and CTP (3 μmol).

EXAMPLE 5

The library from example 4 is modified similarly, but with a nucleoside and nucleoside analog triphosphate pool comprised of 5-(3-mercaptopropyn-1-yl)-2'-deoxyuridine triphosphate (500 nmol), ATP (3 μmol), GTP (3 μmol), and TTP (3 μmol).

What is claimed is:

1. An improvement in a method for creating a ligand for a target compound, said method comprising:

a) synthesizing a mixture of oligonucleotides from nucleotide building blocks each of the oligonucleotides having a region of randomized sequence, b) contacting said mixture with the target, wherein oligonucleotides having an increased affinity to the target relative to others in the mixture may be partitioned from the remainder of the mixture, c) partitioning the oligonucleotides with increased affinity from the other oligonucleotides in the mixture, d) amplifying the oligonucleotides having increased affinity in vitro to yield a mixture of oligonucleotides enriched in those with increased affinity for said target, wherein the improvement comprises including among said nucleotide building blocks those carrying nucleobases selected from the group consisting of

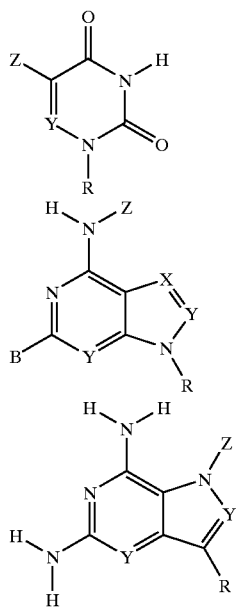

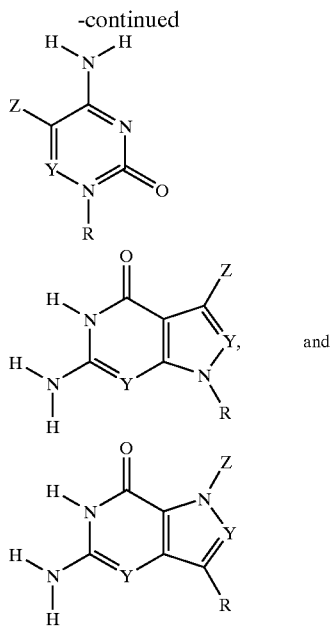

wherein —R designates the point of attachment to the ribose or 2'-deoxyribose ring, B is selected from the group consisting of —H or —NH$_2$, X is either a nitrogen atom or a carbon atom bearing a substituent Z, Z is an unfunctionalized lower alkyl, alkynyl, or alkyl-alkynyl chain, or a lower alkyl, alkynyl, or alkyl-alkynyl chain bearing an amino, carboxyl, hydroxy, thiol, aryl, indole, or imidazoyl group, Y is either N or CH, and the ring contains no more than three nitrogens consecutively bonded.

2. The improvement of claim 1 wherein said nucleobase is selected from the group consisting of

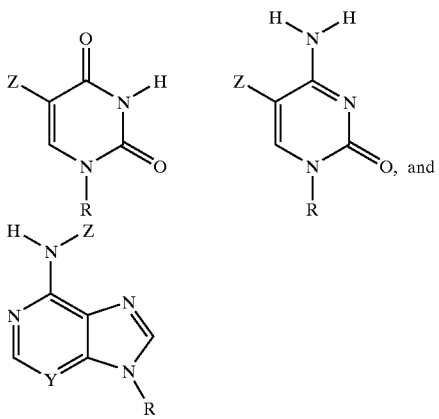

wherein —R designates the point of attachment to the ribose or 2'-deoxyribose ring, and wherein Z is selected from the group consisting of —C≡C—CH$_2$—NH$_2$, —C≡C—CH$_2$—SH, —CH$_2$CH$_2$CH$_2$—NH$_2$, —CH$_2$CH$_2$CH$_2$—SH, —CH$_2$—NH$_2$, —CH$_2$—SH—, CH$_2$CH$_2$—NH$_2$, —CH$_2$CH$_2$—SH, —CH$_2$CH$_2$CH$_2$-imidazole, —CH$_2$CH$_2$-imidazole, lower alkyl, —CH$_2$-imidazole, and —CH$_2$CH$_2$CH$_2$CH$_2$CH$_2$CH$_2$—NH$_2$.

3. An improvement in a method for creating a catalyst for a preselected reaction, said method comprising:

a) synthesizing a mixture of oligonucleotides from nucleotide building blocks each having a region of randomized sequence b) incubating said mixture under conditions where oligonucleotides that catalyze said reaction undergo as a result of their catalytic activity a chemical transformation that makes them preferentially separable from other oligonucleotides in the mixture having less catalytic activity, c) separating die oligonucleotides with increased catalytic activity from the other oligonucleotides in the mixture d) copying the oligonucleotides having increased catalytic activity in vitro to yield a mixture of oligonucleotides enriched in those with increased catalytic activity, wherein the improvement comprises including among said nucleotide building blocks those carrying nucleobases selected from the group consisting of

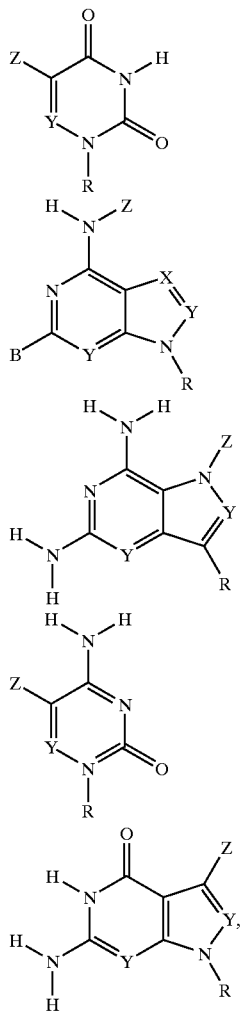

and

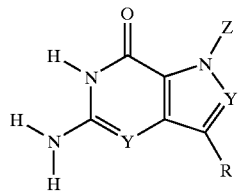

wherein —R designates the point of attachment to the ribose or 2'-deoxyribose ring, B is selected from the group consisting of —H or —NH$_2$, X is either a nitrogen atom or a carbon atom bearing a substituent Z, Z is an unfunctionalized lower alkyl, alkynyl, or alkyl-alkynyl chain, or a lower alkyl, alkynyl, or alkyl-alkynyl chain bearing an amino, carboxyl, hydroxy, thiol, aryl, indole, or imidazoyl group, Y is either N or CH, and the ring contains no more than three nitrogens consecutively bonded.

4. The improvement of claim 3, wherein said nucleobase is selected from the group consisting of

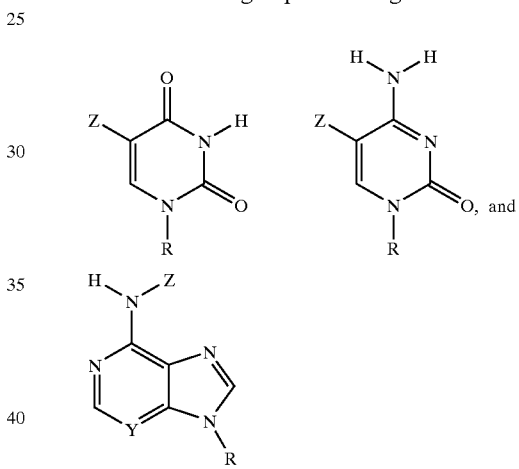

wherein —R designates the point of attachment to the ribose or 2'-deoxyribose ring, and wherein Z is selected from the group consisting of —C≡C—CH$_2$—NH$_2$, —C≡C—CH$_2$—SH, —CH$_2$CH$_2$CH$_2$—NH$_2$, —CH$_2$CH$_2$CH$_2$—SH, —CH$_2$—NH$_2$, —CH$_2$—SH—, CH$_2$CH$_2$—NH$_2$, —CH$_2$CH$_2$—SH, —CH$_2$CH$_2$CH$_2$-imidazole, —CH$_2$CH$_2$-imidazole, lower alkyl, —CH$_2$-imidazole, and —CH$_2$CH$_2$CH$_2$CH$_2$CH$_2$CH$_2$—NH$_2$.

* * * * *